US010018602B2

United States Patent
Ueno et al.

(10) Patent No.: US 10,018,602 B2
(45) Date of Patent: Jul. 10, 2018

(54) MULTICOMPONENT QUANTITATIVE ANALYSIS METHOD USING CHROMATOGRAPHY

(71) Applicants: SHIMADZU CORPORATION, Kyoto-shi, Kyoto (JP); AICHI PREFECTURAL GOVERNMENT, Nagoya-shi, Aichi (JP)

(72) Inventors: Eiji Ueno, Tokai (JP); Riki Kitano, Kyoto (JP); Haruhiko Miyagawa, Kyoto (JP)

(73) Assignees: SHIMADZU CORPORATION, Kyoto-shi, Kyoto (JP); AICHI PREFECTURAL GOVERNMENT, Nagoya-shi, Aichi (JP)

( * ) Notice: Subject to any disclaimer, the term of this patent is extended or adjusted under 35 U.S.C. 154(b) by 266 days.

(21) Appl. No.: 15/032,394

(22) PCT Filed: Oct. 27, 2014

(86) PCT No.: PCT/JP2014/078476
§ 371 (c)(1),
(2) Date: Apr. 27, 2016

(87) PCT Pub. No.: WO2015/064530
PCT Pub. Date: May 7, 2015

(65) Prior Publication Data
US 2016/0266074 A1    Sep. 15, 2016

(30) Foreign Application Priority Data
Oct. 28, 2013 (JP) .................................. 2013-223117

(51) Int. Cl.
*G01N 30/06* (2006.01)
*G01N 30/88* (2006.01)
(Continued)

(52) U.S. Cl.
CPC ............ *G01N 30/06* (2013.01); *B01J 20/283* (2013.01); *G01N 30/48* (2013.01); (Continued)

(58) Field of Classification Search
CPC ..... G01N 30/06; G01N 30/88; G01N 30/8665
See application file for complete search history.

(56) References Cited

U.S. PATENT DOCUMENTS

| 5,411,707 A * | 5/1995 | Hiatt ........................ B01D 3/10 |
| | | 422/68.1 |
| 5,536,301 A * | 7/1996 | Lansbarkis ............ B01D 53/02 |
| | | 95/117 |
| 9,222,921 B2 * | 12/2015 | Saini ...................... G01N 30/88 |

FOREIGN PATENT DOCUMENTS

| JP | 2003-342291 A | 12/2003 |
| WO | 2008/154619 A1 | 12/2008 |
| WO | 2011/116028 A1 | 9/2011 |

OTHER PUBLICATIONS

Communication dated Jul. 21, 2016, from the European Patent Office in counterpart European application No. 14859018.5.
(Continued)

*Primary Examiner* — Blake A Tankersley
(74) *Attorney, Agent, or Firm* — Sughrue Mion, PLLC

(57) ABSTRACT

A number of analytes are divided into groups based on at least either the elution position determined by silica gel column chromatography under the same condition or the partition ratio in a hexane-acetonitrile partition method. To each group, a compound obtained by labeling one of the compounds in the group by deuterium and/or carbon is assigned as the surrogate. After those surrogates are added as internal standard substances to a standard sample for the creation of calibration curves, a GC/MS analysis for the sample is performed and a calibration curve is created for each analyte. In the measurement of an unknown sample, the (Continued)

same set of surrogates are added to the sample and the GC/MS analysis is performed. A quantitative determination processor determines the quantity of each analyte by comparing a peak area ratio calculated from the analysis result with a calibration curve read from the database.

4 Claims, 4 Drawing Sheets

(51) Int. Cl.
    *G01N 30/86*     (2006.01)
    *B01J 20/281*     (2006.01)
    *B01J 20/283*     (2006.01)
    *G01N 30/72*     (2006.01)
    *G01N 30/00*     (2006.01)

(52) U.S. Cl.
    CPC ......... *G01N 30/8665* (2013.01); *G01N 30/88* (2013.01); *B01J 2220/54* (2013.01); *G01N 30/7206* (2013.01); *G01N 2030/486* (2013.01)

(56) References Cited

OTHER PUBLICATIONS

Written Opinion for PCT/JP2014/078476 dated Jan. 27, 2015. [PCT/ISA/237].
International Search Report for PCT/JP2014/078476 dated Jan. 27, 2015.

* cited by examiner

MULTICOMPONENT QUANTITATIVE ANALYSIS METHOD USING CHROMATOGRAPHY

CROSS REFERENCE TO RELATED APPLICATIONS

This application is a National Stage of International Application No. PCT/JP2014/078476 filed Oct. 27, 2014, claiming priority based on Japanese Patent Application No. 2013-223117 filed Oct. 28, 2013, the contents of all of which are incorporated herein by reference in their entirety.

TECHNICAL FIELD

The present invention relates to a quantitative analysis method for quantitatively determining the concentration of a compound in a sample using a chromatograph, such as a gas chromatograph or liquid chromatograph, and more specifically, to a multicomponent quantitative analysis method for a simultaneous multicomponent analysis in which the concentrations of a number of compounds contained in a sample are quantitatively determined on the basis of the result of a single chromatographic analysis.

BACKGROUND ART

In the quantitative determination of the concentration of a compound in a sample using a chromatograph, such as the gas chromatograph (GC) or liquid chromatograph (LC), the calibration curve method is normally used. The calibration curve method is a quantitative determination method in which the concentration is calculated from an analysis result with reference to a previously created calibration curve. Examples of this technique include the external standard method and internal standard method.

In the external standard method, a standard sample containing an analyte is prepared. A plurality of standard samples with different concentrations of the analyte are prepared, and a measurement is performed for each standard sample to collect data. A chromatogram is created from the collected data, and a peak originating from the analyte is located on the chromatogram. The area (or height) of this peak is computed, and a calibration curve showing the relationship between the peak area value and the concentration is created. After the measurement of an unknown sample is performed, the area value of the peak originating from the analyte on the chromatogram obtained by the measurement is computed. By comparing this area value with the calibration curve, the concentration of the analyte in the unknown sample is calculated. By the external standard method, a highly accurate quantitative determination can be achieved as long as there is no influence of foreign substances or other unfavorable factors. However, the method inconveniently requires the standard sample to be prepared for each analyte and the calibration curve to be created based on the result of the measurement of each standard sample.

On the other hand, in the internal standard method, a fixed quantity of internal standard substance whose retention time is as close to the analyte as possible within the range where the internal standard substance can be separated from the analyte by a chromatograph (and additionally, by the difference in their mass-to-charge ratios if a mass spectrometer is used as the detector) is added to the standard sample for the creation of calibration curves, and a measurement for the sample is performed to collect data. On a chromatogram created from those data, both the peak originating from the internal standard substance and the peak originating from the substance for the creation of calibration curves appear. The areas (or heights) of these peaks are individually computed, and a calibration curve showing the relationship between the peak area ratio and the concentration is created. In the measurement of an unknown sample, the fixed quantity of the same internal standard substance is added to the unknown sample, and the peak area ratio is computed from the chromatogram obtained by the measurement of the sample. By comparing this area ratio with the calibration curve, the concentration of the analyte in the unknown sample is calculated. According to the internal standard method, it is possible to avoid measurement errors due to various factors, such as the variation in the amount of sample injected into the chromatograph or the vaporization of the sample solvent.

In the testing of residual agricultural chemicals or environmental pollutants the screening of drugs and poisons or other similar measurements, it s necessary to determine the quantities of tens of compounds, or even hundreds of compounds with different physical properties based on the result of a single measurement. For such a simultaneous multicomponent analysis, a gas chromatograph mass spectrometer (GC/MS) or liquid chromatograph mass spectrometer (LC/MS), both of which are capable of separating components according to their mass-to-charge ratios in addition to the temporal separation of the components by the chromatograph, is commonly used. In the case of the simultaneous multicomponent analysis, it is practically impossible to prepare a standard sample, perform a measurement and create a calibration curve for each of all of the analytes from the viewpoints of the cost and efficiency of the analysis. Accordingly, it is impractical to adopt the quantitative determination which employs the external standard method.

Even in the case of the quantitative determination employing the internal standard method, or the semi-quantitative determination, it is considerably difficult to prepare an internal standard substance for each analyte. A conventional and common procedure for addressing this problem is as follows: The plurality of analytes are divided into groups each of which includes analytes whose retention times are close to each other. For each group, an appropriate kind of compound, or more specifically, a physically and chemically stable compound which is as close to that group as possible in terms of retention time, is assigned as the internal standard substance, and this internal standard substance is used in the quantitative determination by the internal method.

Another factor to be considered is that certain kinds of analytes are easily desorbed or decomposed during the analysis; for example, such a situation can occur in a GC/MS depending on the condition of the injection-port insert provided at the inlet of the column, the column, the ion source or other devices. The internal standard substance which is physically and chemically stable barely undergoes such desorption or decomposition. Therefore, if such an internal standard substance is used in the quantitative determination employing the internal standard method, it is often the case that a variation of the quantitative value due to the aforementioned factor cannot be corrected. In particular, such a situation is noticeable in the simultaneous multicomponent analysis of agricultural chemicals or similar substances which vary in physical properties including the polarity. Such a variation in the quantitative value does not only occur due to the previously described factors which depend on the condition of the devices; it also frequently occurs due to the loss of a portion of the analyte as a result of a sample pretreatment operation, such as the extraction from the sample, purification, condensation or constant-volume sampling of the analyte.

As a technique for correcting the variation in the quantitative value due to the various aforementioned factor (particularly, those associated with the sample pretreatment operation), a surrogate method has conventionally been used. In the surrogate method, a substance having similar physical properties to the analyte is selected as the surrogate. A known amount of surrogate is added to the sample before this sample is pretreated. After the pretreatment operation is completed, the recovery percentage of the surrogate in the obtained sample is determined and the quantitative value is corrected on the premise that the analyte is also recovered by the same percentage (for example, see Patent Literature 1). The surrogate should preferably be a compound which is separable from the analyte and yet is as similar to the analyte as possible in terms of the physical properties. In general, a compound which is structurally identical to the analyte and is labeled by a stable isotope (typically, deuterium) is used.

Normally, the internal standard substance is added to the sample after the pretreatment operation. However, it is also common to utilize the surrogate, which is added before the pretreatment operation, as the internal standard substance to create a calibration curve and perform the quantitative determination by the internal standard method. This technique enables a highly accurate quantitative determination which reflects the loss of the compound that occurs in the stage of the sample pretreatment operation.

However, in the simultaneous multicomponent analysis, it is practically impossible to prepare one surrogate for each of the analytes whose number exceeds several hundreds. The technique of assigning the internal standard substances as used in the previously described normal mode of simultaneous multicomponent analysis may also be similarly applicable in the case of utilizing the surrogates as the internal standard substances; i.e. it may be possible to divide analytes into groups and assign an appropriate kind of surrogate to each group. However, it is difficult to properly make such an assignment.

CITATION LIST

Patent Literature

SUMMARY OF INVENTION

Technical Problem

The present invention has been developed in view of the previously described problems. Its objective is to provide a multicomponent quantitative analysis method which can accurately determine quantities by cancelling the influence of various factors, such as the loss of compounds in the stage of the sample pretreatment operation or during the analysis, without requiring the preparation of one internal standard substance or surrogate for each of all of the analytes even in the case of a simultaneous multicomponent analysis in which the quantities of more than hundreds of analytes need to be determined.

Solution to Problem

The present invention developed for solving the previously described problem is a multicomponent quantitative analysis method for determining the quantities of a number of compounds contained in a sample using a chromatograph, the method including the following steps:

at least a portion of a number of analytes which may possibly be contained in a sample to be analyzed is divided into a plurality of groups based on at least either an elution position determined by silica gel column chromatography under the same condition or a partition ratio in a hexane-acetonitrile partition method, and a different surrogate is designated for each group;

the surrogate is added to a standard sample for the creation of calibration curves as a common internal standard substance for analytes included in each group, a chromatographic analysis of the standard sample is performed, and a calibration curve to be used for a quantitative determination of the analytes by an internal standard method is created based on the result of the chromatographic analysis; and in a quantitative determination of analytes contained in an unknown sample, the plurality of surrogates are added to the unknown sample, a chromatographic analysis of the unknown sample is performed, and the result of this chromatographic analysis is compared with the corresponding calibration curves to determine the quantities of the analytes.

The "chromatograph" in the present invention is either a gas chromatograph or a liquid chromatograph, including chromatograph mass spectrometers which use a mass spectrometer as the detector.

The term "elution position" in the silica gel column chromatography means an "elution fraction" in the case of collecting individual fractions of the eluate from the column while continuously passing a plurality of solvents having different polarities down the column.

The phrase "a number of" used in the previous description, as in "a number of compounds" or "a number of analytes", is not intended to define any specific lower limit. However, it is ordinarily reasonable to consider that there should be at least ten compounds, and normally tens of compounds or even more, taking into account the number of compounds to be covered in a simultaneous multicomponent analysis under normal conditions.

In the multicomponent quantitative analysis method using a chromatograph according to the present invention, a number of analytes which may possibly be contained in a sample to be analyzed are divided into groups according to the degree of similarity or difference in their physical properties, such as the polarity, volatility or decomposability. However, the grouping does not rely on any literature values, such as the octanol-water partition coefficient Log Pow or aqueous solubility; the grouping of the analytes is performed using at least either the elution position determined by an actual silica gel column chromatographic analysis under the same condition or the result of a measurement of the partition ratio in a hexane-acetonitrile partition method. This grouping method attaches importance on the polarity among the physical properties. This is particularly useful for gas chromatographic analyses, because the primary cause of the variation in the quantitative value in the gas chromatographic analysis is the easy adsorption of high-polarity compounds on the active points (e.g. silanol group) which act as the stationary phase in the column.

In general, the use of literature values often leads to an improper grouping since many of those values are obtained under different conditions. By contrast, when the grouping is performed in the previously described manner based on the elution position under the same condition and/or the measured value of the partition ratio, the analytes will be properly grouped based on their polarities.

More specifically, in one preferable mode of the multicomponent quantitative analysis method according to the present invention, at least a portion of a number of analytes which may possibly be contained in a sample to be analyzed is divided into a plurality of groups based on the relative values of the elution position of each analyte and the elution positions of the surrogates and/or the relative values of the partition ratio of each analyte and the partition ratios of the surrogates, and the surrogate for each group is designated. According to this mode, for each group which is primarily formed according to the polarity, an appropriate surrogate for the quantitative determination of the analytes included in that group, i.e. a surrogate which is approximately equal to the analytes in the group in terms of the recovery percentage in the sample pretreatment operation as well as in terms of the degree of loss which occurs due to the adsorption or other causes during the analysis, is selected, and a calibration curve using that surrogate as the internal standard substance is created. Therefore, although the surrogate is not assigned to each analyte but to each group, a high level of quantitative accuracy can be realized.

In one preferable mode of the multicomponent quantitative analysis method according to the present invention, the surrogate assigned to each group is a compound obtained by the stable-isotope labeling of a compound which is one of the analytes included in that group.

In the multicomponent quantitative analysis method according to the present invention, the addition of the surrogate to the sample in the process of creating the calibration curve and in the measurement of an unknown sample can be achieved by adding the surrogate either as a syringe spike or as a clean-up spike. It should be noted that, in the measurement of an unknown sample with the surrogate added as the clean-up spike, the quantitative determination must be performed using the calibration curve which was created when the surrogate was added as the clean-up spike. Similarly, in the measurement of an unknown sample with the surrogate added as the syringe spike, the quantitative determination must be performed using the calibration curve which was created when the surrogate was added as the syringe spike.

Advantageous Effects of the Invention

With the multicomponent quantitative analysis method using a chromatograph according to the present invention, it is possible to correct the variation in the signal intensity for the analyte due to a change in the condition of a device (or other factors) and realize a highly accurate quantitative determination by using a much smaller number of surrogates than the total number of the analytes which need to be quantitatively analyzed based the result of a single chromatographic analysis; for example, only tens of surrogates need to be prepared for hundreds of analytes. By adding the surrogates to the sample before the sample pretreatment operation, i.e. by adding the surrogates as the clean-up spike, it is possible to additionally correct the variation in the quantitative value due to the loss of the sample in the stage of the sample pretreatment operation (or other factors) and enable an even more accurate quantitative determination.

DESCRIPTION OF EMBODIMENTS

The multicomponent quantitative analysis method according to the present invention is hereinafter described in detail with reference to the attached drawings.

Figure 1:
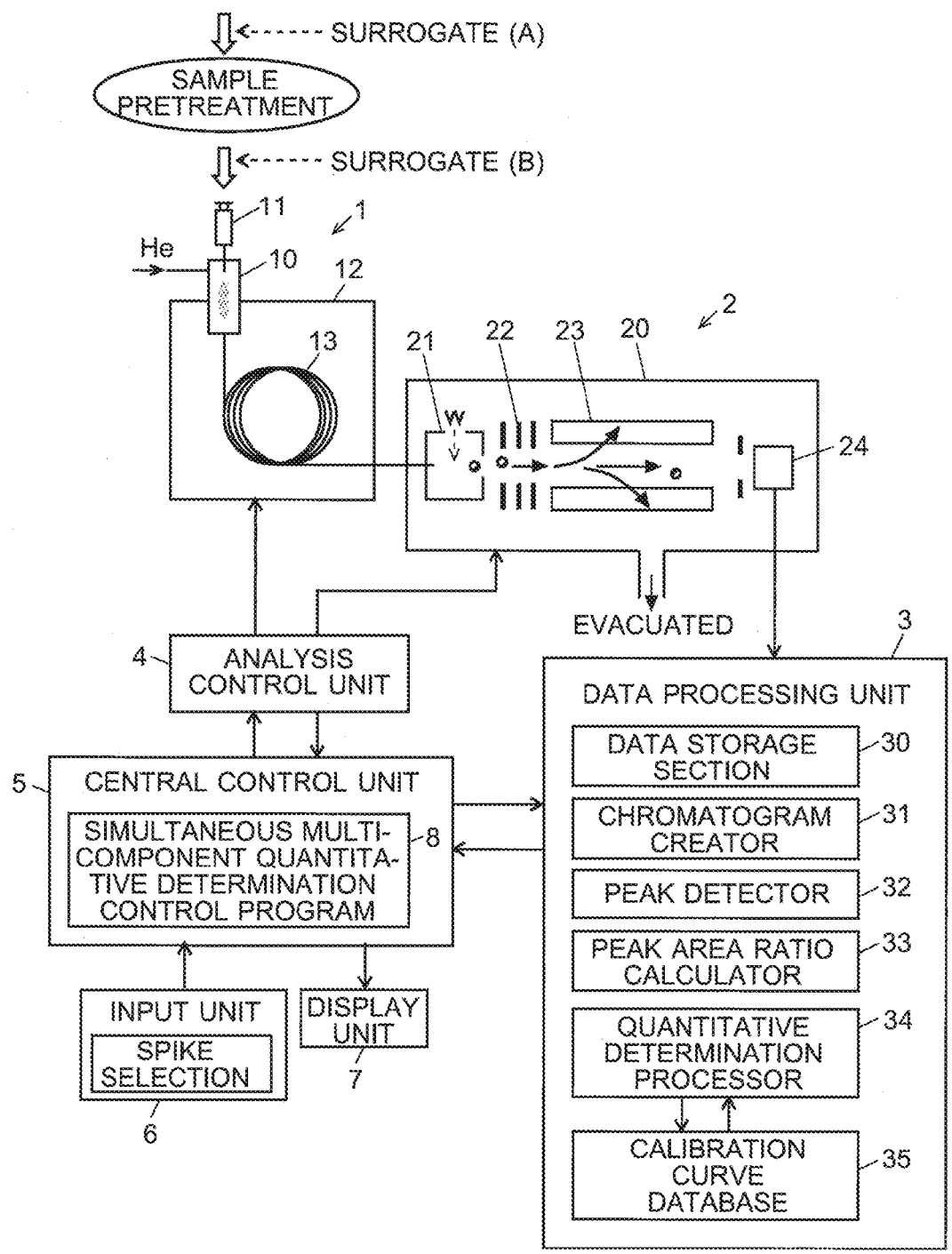
FIG. 1 is a schematic configuration diagram of one embodiment of a GC/MS which carries out a multicomponent quantitative analysis method according to the present invention.

FIG. 1 is a schematic configuration diagram of one embodiment of a GC/MS which carries out the multicomponent quantitative analysis method according to the present invention.

This GC/MS includes a gas chromatograph (GC) 1, mass spectrometer 2, data processing unit 3, analysis control unit 4, central control unit 5, input unit 6, and display unit 7. The GC 1 includes a sample vaporization chamber 10 for vaporizing a small amount of liquid sample, a micro-syringe 11 for injecting the liquid sample into the sample vaporization chamber 10, a column 13 for temporally separating the components of the sample, and a column oven 12 for controlling the temperature of the column 13. The mass spectrometer 2 includes an analysis chamber 20 evacuated by a vacuum pump (not shown). This Chamber contains an ion source 21 for ionizing compounds to be analyzed by an appropriate ionization method (e.g. electron ionization), an ion lens 22 for transporting ions while converging them, a quadrupole mass filter 23 composed of four rod electrodes, and a detector 24 for producing, as the detection signal, an ion strength signal corresponding to the amount of incoming ions.

The data processing unit 3, which is fed with the ion strength data by the detector 24, includes a data storage section 30, chromatogram creator 31, peak detector 32, peak area ratio calculator 33, quantitative determination processor 34, and calibration curve database 35 as its functional blocks. As will be described later, the data processing unit 3 quantitatively determines the concentrations of a number of analytes contained in a sample.

The analysis control unit 4 has the function of controlling the operations of the GC 1 and the mass spectrometer 2 under the command of the central control unit 5. The central control unit 5 is responsible for the general control of the entire system in addition to the user interface through the input unit 6 and display unit 7. The central control unit 5 includes a storage device, which holds a simultaneous multicomponent quantitative determination control program 8 for carrying out a characteristic control for a simultaneous multicomponent analysis (which will be described later). According to this program 8, the CPU (and other devices controls each section of the system via the analysis control unit 4 to perform measurements and data processing necessary for simultaneously determining the quantities of a number of analytes contained in a sample.

The central control unit 5 and the data processing unit 3 can be configured, for example, on a personal computer prepared as a hardware resource, with their respective functions realized by running, on this computer, a dedicated controlling and processing software program previously installed on the same computer. In this case, the input unit 6 includes a keyboard and pointing device e.g. mouse) annexed to the computer. The display unit 7 is the display monitor of the computer.

The basic operations for the GC/MS analysis in the GC/MS of the present embodiment are hereinafter schematically described.

When a small amount of liquid sample is dropped from the micro-syringe 11 into the sample vaporization chamber 10, the liquid sample quickly vaporizes within the sample vaporization chamber 10. Various kinds of substances in the sample are carried by the carrier gas (e.g. helium) into the column 13. While the sample is passing through the column 13, the substances in the sample are individually delayed by different amounts of time and reach the exit port of the column 13. The column oven 12 is controlled so to maintain the temperature at an almost fixed level or increase the temperature according to a predetermined temperature profile. The ion source 21 in the mass spectrometer 2 sequentially ionizes the substances in the gas supplied from the exit port of the column 13.

The analysis control unit 4 applies, to each rod electrode of the quadrupole mass filter 23, a specific form of voltage which allows the passage of an ion having a specific mass-to-charge ratio. Therefore, among the various ions originating from the compounds introduced into the ion source 21, only an ion having a specific mass-to-charge ratio is allowed to pass through the quadrupole mass filter 23 and reach the detector 24, which sends a signal corresponding to the amount of ion to the data processing unit 3. In the present case, the kinds of analytes are previously known (although it is unknown whether or not they are actually contained in the sample). For example, in the common testing of the residual agricultural chemicals in foods, all agricultural chemicals registered in the "Positive List" (which is used in Japan to control foods containing residual agricultural chemicals) should be considered as analytes. Accordingly, the mass-to-charge ratios of the ions to be detected originating from the analytes are previously known, and the retention times for those analytes are also previously known. Therefore, it is possible to completely detect the ions originating from the analytes by conducting the selected ion monitoring (SIM) measurement in the mass spectrometer 2 with the range of the measurement time defined in the vicinity of the retention time for each analyte and the monitored mass-to-charge ratio set at the value corresponding to the analyte.

Figure 2:
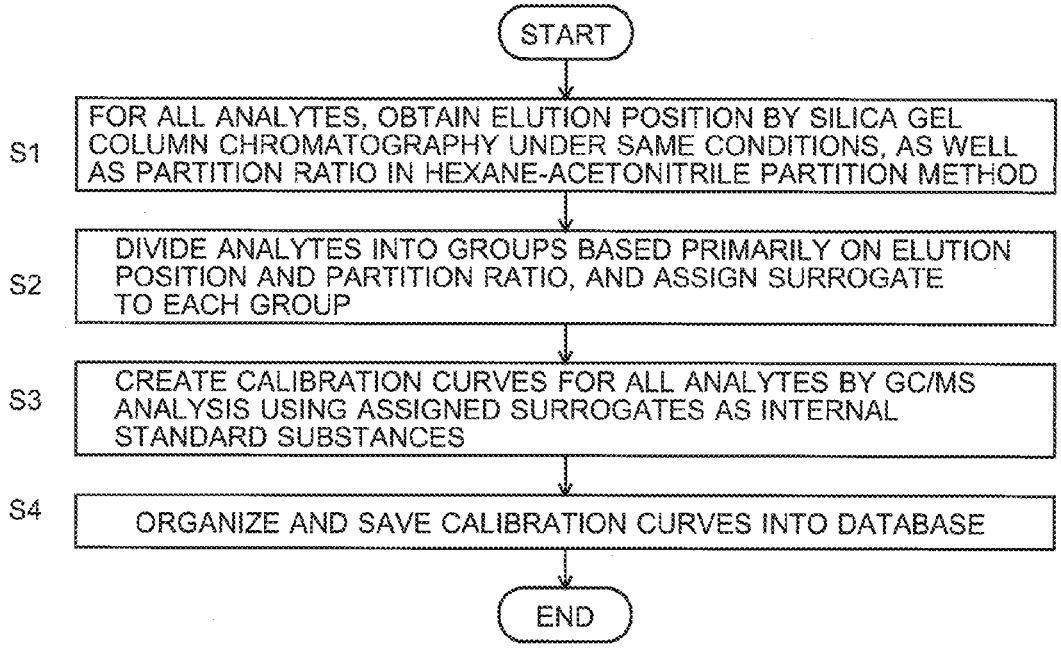
FIG. 2 is a flowchart showing the procedure of creating a calibration curve database in GC/MS of the present embodiment.

To simultaneously determine the quantities of a number of aforementioned kinds of known analytes contained in an unknown sample in the GC/MS of the present embodiment, it is necessary to previously construct the calibration curve database 35 for the quantitative determination which employs the internal standard method. Normally, the calibration curve database 35 is not prepared by users of the system but by the manufacturers selling the system. FIG. 2 is a flowchart showing the procedure of creating the calibration curve database 35.

In the quantitative determination carried out in the GC/MS of the present embodiment, a number of analytes are divided into a plurality of groups, and one surrogate is assigned to each group as the internal standard substance. In general, in a gas chromatograph, high-polarity compounds easily adsorb on the active points (e.g. silanol group) which act as the stationary phase in the column, and this adsorption is the primary cause of the variation in the quantitative value. Therefore, the extent of the variation in the quantitative value mainly depends on the degree of adsorption, i.e. the polarity. Accordingly, by giving the primary attention to the difference in the polarities of the analytes in performing the grouping of a number of analytes, it is possible to easily correct the quantitative value and perform that correction with a high level of accuracy. Examples of the index values showing the polarities of various compounds include the octanol-water partition coefficient Log Pow and aqueous solubility. Those values are available in various pieces of literature. However, it is inappropriate to compare those values with each other, since they are not always obtained under the same conditions. Additionally, there are many substances for which such literature values are not provided.

Accordingly, in order to properly perform the grouping of all analytes based primarily on the polarity, a silica gel column chromatographic measurement is performed for all an analytes under the same condition to determine the elution position elution fraction) for each analyte. Additionally, the partition ratio in the hexane-acetonitrile partition method is measured for all analytes (Step S1).

The partition ratio in the hexane-acetonitrile partition method can be determined by shaking a sample liquid containing a known amount of each analyte with predetermined quantities of hexane and acetonitrile added, collecting the fraction of the acetonitrile layer (and/or hexane layer), determining the quantity of the analyte in this acetonitrile layer (and/or hexane layer), and calculating the partition ratio from the obtained result. Specifically, in the method of the present embodiment, 25 mL of acetonitrile-saturated n-hexane, 0.2 mL of standard solution, and 50 mL of n-hexane-saturated acetonitrile are sequentially put in a 100-mL separating funnel. The liquid is shaken for 30 minutes and then left at rest for 30 minutes. Subsequently, the lower layer is collected as acetonitrile fraction #1. Meanwhile, 50 mL of n-hexane-saturated acetonitrile is additionally put in the upper layer. The liquid is once more shaken for 30 minutes and then left at rest for 30 minutes. Subsequently, the lower layer is collected as acetonitrile fraction #2, and the upper remaining layer is collected as hexane fraction. A quantitative analysis is performed for each of the obtained fractions, i.e. acetonitrile fraction #1, acetonitrile fraction #2 and hexane fraction. The partition ratio in the hexane-acetonitrile partition method is eventually determined from the result of this analysis.

Meanwhile, for each group including the analytes having similar physical properties including the polarity, a surrogate that seems to be suited to the group is designated. For each surrogate, the elution position by silica gel column chromatography and the partition ratio in the hexane-acetonitrile partition method are determined by actual measurements in the previously described manner. As the surrogate, a compound obtained by the stable-isotope labeling of a compound selected from the analytes, or more specifically, a compound labeled by deuterium or carbon 13, can be used. The selection may be appropriately made taking into account the purchasability, inexpensiveness and so on. Based on the relative value of the elution position of each individual analyte and those of the surrogates, the relative value of the partition ratio of each individual analyte and those of the surrogates, well as other information, a number of analytes are divided into groups and an appropriate surrogate is assigned to each group (Step S2).

Actually, the task of Step S2 is to some extent conducted by trial and error. Reducing the size of the individual groups makes it easier to improve the quantitative accuracy. However, it also imposes a significant financial burden on users by requiring the preparation of a greater number of surrogates in the measurement of a real sample. Additionally, it increases the probability of some of the surrogates being unavailable and thereby preventing the quantitative determination for some of the analytes. Accordingly, in normal situations, the grouping should be made so that each group includes approximately ten to several tens of analytes. For example, in the simultaneous analysis of hundreds of analytes, the number of groups should be approximately within a range from ten to several tens of groups. Such a moderate way of grouping will not impose a significant burden on users in the preparation of the surrogates, while ensuring a high level of quantitative accuracy for an analyte for which the quantitative determination is performed using an internal standard substance which is not a compound obtained by the deuterium substitution of the analyte itself but a compound obtained by the deuterium substitution of another compound.

After the grouping of a number of analytes and the selection of the surrogates for the groups in Step S2 is completed, the surrogates are added as the internal standard substances to a standard sample for the creation of calibration curves, and a GC/MS analysis is performed for this sample to create a calibration curve for each of all analytes (Step S3). This GC/MS analysis does not need to be performed using the system which will be actually offered to users e.g. it may be performed using another system of the same model.

The addition of the surrogates to the standard sample for the creation of calibration curves can be performed in two forms, i.e. as a syringe spike or as a clean-up spike. The calibration curve for the same analyte changes depending on which form is chosen. Accordingly, for each of the syringe and clean-up spikes, the GC/MS analysis is performed and a calibration curve is created for each analyte.

Specifically, in the case of the syringe spike, surrogates are added to the sample solution which has undergone the sample pretreatment operation (this addition is made at the stage labeled "Surrogate (B)" in FIG. 1), and this sample solution is injected through the micro-syringe into the sample vaporization chamber to perform the GC/MS analysis. On the other hand, in the case of the clean-up spike, surrogates are added to a sample solution before the sample pretreatment operation is performed, i.e. to an extracted liquid from the sample or an unrefined sample liquid (this addition is made at the stage labeled "Surrogate (A)" in FIG. 1). Subsequently, the sample pretreatment operation is performed and the thereby obtained sample solution is injected through the micro-syringe into the sample vaporization chamber to perform the GC/MS analysis. With regards to the clean-up spike, it should be noted that the calibration curve changes depending on the content of the sample pretreatment operation, and therefore, it is necessary to perform the GC/MS analysis and create the calibration curve for each content of the sample pretreatment operation which will be performed in the actual quantitative analysis.

After the calibration curves for all analytes and for each of the syringe and clean-up spikes are created in the previously described manner, the created curves are organized into a database, whereby the calibration curve database 35 is constructed (Step S4). The calibration curve database 35 may have any data structure which allows an appropriate calibration curve to be extracted according to the selection of either the syringe spike or clean-up spike, specification of the content of the sample pretreatment operation (in the case of the clean-up spike) and indication of the kind of analyte.

Figure 3:
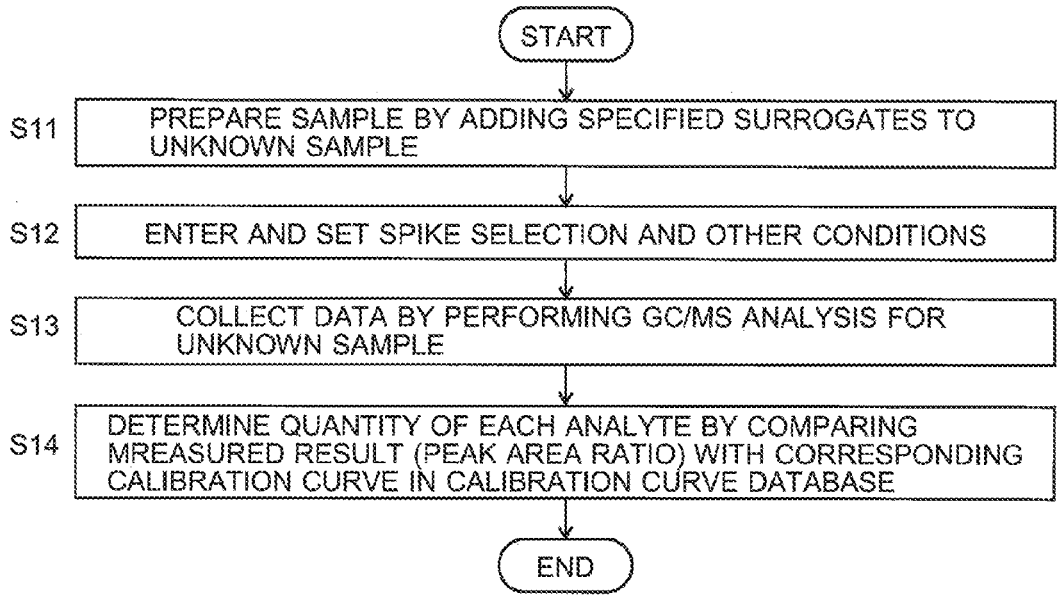
FIG. 3 is a flowchart showing the procedure of the quantitative determination of analytes in a real sample using the GC/MS of the present embodiment.

On the user's side, an analysis for determining the quantities of the analytes in an unknown sample of interest is performed using the GC/MS having the appropriate calibration curve database 35 constructed in the previously described manner. The procedure and the system operation for this analysis are hereinafter described with reference to the flowchart shown in FIG. 3.

For example, in the simultaneous screening of residual agricultural chemicals, the kinds of surrogates to be added are previously specified. The analysis operator prepares those kinds of surrogates and adds them to the unknown sample as either the clean-up spike or syringe spike. In the case of the clean-up spike, after the various surrogates are added to the unknown sample (at the stage labeled "Surrogate (A)" in FIG. 1), a predetermined sample pretreatment operation (e.g. the extraction, purification, condensation, or constant-volume sampling of some of the analytes) is performed to prepare a sample to be analyzed. The prepared sample is put in the micro-syringe 11. In the case of the syringe spike, after the aforementioned sample pretreatment operation is completed, the various surrogates are added to the pretreated sample (at the stage labeled "Surrogate (13)" in FIG. 1) to eventually obtain a sample to be put in the micro-syringe 11 as the target of the analysis (Step S11).

The analysis operator using the input unit 6 enters and sets the selection of either the clean-up spike or syringe spike as one of the measurement conditions. In the case of the clean-up spike, the content of the sample pretreatment operation which is planned to be used (or has been performed) should also be entered and set (Step S12). It is convenient to configure the system so that the analysis operator can perform these entering and setting tasks by selecting one of the prepared choices. Subsequently, the analysis operator also enters and sets various other measurement conditions, and commands the initiation of the analysis. It should be noted that, in some cases, the SIM measurement targets (i.e. the mass-to-charge ratios and retention times) in the mass spectrometer 2 are also prescribed, as in the case of the simultaneous screening of the residual agricultural chemicals according to the Positive List. Therefore, the system may also be configured an that most of the measurement conditions can be automatically set by the analysis operator simply selecting the type of quantitative analysis, e.g. "the simultaneous screening of residual agricultural chemicals".

Upon receiving the command to initiate the analysis control unit 4 sends predetermined control signals to the GC 1 and the mass spectrometer 2 according to the simultaneous multicomponent quantitative determination control program 8, whereby the GC/MS analysis is initiated. That is to say, the sample solution with the various surrogates mixed is injected from the micro-syringe 11 into the sample vaporization chamber 10, and the compounds in the sample are introduced into the column 13. While passing through this column 13, the temporal separation occurs among different kinds of surrogates as well as between the surrogates and the analytes. If there are two substances which cannot be fully separated by the column 13, they can still be adequately distinguished from each other since there is a significant difference in the mass-to-charge ratios of the ions which are designated as the targets for detecting the respective substances.

The data obtained by the GC/MS analysis using the GC 1 and the mass spectrometer 2, i.e. the ion strength data which reflect the amount of ions originating from the substances contained in the sample, are temporarily stored in the data storage section 30. After the analysis is completed, the chromatogram creator 31 in the data processing unit 3 reads the data to be processed from the data storage section 30.

Based on the read data, it creates the mass chromatogram at the specific mass-to-charge ratio characteristic of each surrogate or analyte. The peak detector 3 locates a peak in the vicinity of the previously set retention time on each of the mass chromatograms and calculates the area value of the detected peak. Additionally, for each analyte, the peak area ratio calculator 33 computes the ratio between the peak area value of the peak on the mass chromatogram corresponding to the analyte concerned and that of the peak on the mass chromatogram corresponding to the surrogate assigned to the group which includes that analyte.

The quantitative determination processor 34 reads, from the calibration curve database 35, a calibration curve corresponding to the type of spike and the content of the sample pretreatment operation (in the case of the clean-up spike) specified by the analysis operator in Step S12 as well as to the kind of analyte. It compares the calculated peak area ratio with the calibration curve to determine the concentration of the analyte of interest. Such a process of determining the concentration with reference to the calibration curve is similarly performed for each analyte of interest until the quantities of all analytes are determined (Step S14). Ultimately, the result of the quantitative determination of each analyte is displayed on the screen of the display unit 7 along with the result of the GC/MS analysis, the mass chromatogram.

According to the previously described quantitative analysis method, even when there are hundreds of kinds of analytes whose quantities need to be determined, it is unnecessary to prepare a standard sample containing all of those analytes; the analysis operator use only needs to prepare at most tens of kinds of surrogates. Accordingly, the financial burden is dramatically reduced. The surrogates are added as either the syringe spike or clean-up spike. Therefore, even there is the loss of a substance in the process of the GC/MS analysis or the loss of a substance at the stage of the sample pretreatment operation (the latter loss occurs only in the case of the clean-up spike), the loss can be corrected and a highly accurate quantitative value can be obtained. Additionally, in the GC/MS of the previous embodiment, all calibration curves necessary for the quantitativ determination are stored in the calibration curve database 35. Therefore, the analysis operator does not need to manually create the calibration curves and can efficiently proceed with the work for the quantitative analysis.

EXAMPLE

[Example of Measurement of Residual Agricultural Chemicals]

As one application example of the previously described multicomponent quantitative analysis method using the GC/MS, a measurement was performed on diazinon and pyridaben, both of which are subject to control as residual agricultural chemicals. The result of the measurement was as follows.

Diazinon is classified into organophosphorus pesticides, while pyridaben is classified into nitrogen-containing pesticides. Both substances include a ring system consisting of the benzene ring with two neighboring carbon atoms replaced by nitrogen atoms, and therefore have similar polarities. Specifically, diazinon and pyridaben have the same elution position in the silica gel column chromatography. Therefore, the two substances are classified into the same group. The surrogate selected for this group is diazinon-d10, i.e. the deuterated diazinon.

In this case, the quantitative determination for diazinon is performed using, as the internal standard substance, a compound obtained by the deuteration of diazinon itself, while the quantitative determination for pyridaben is performed using, as the internal standard substance, a compound obtained by the deuteration of not pyridaben itself but a different compound having similar physical properties.

Figure 4:
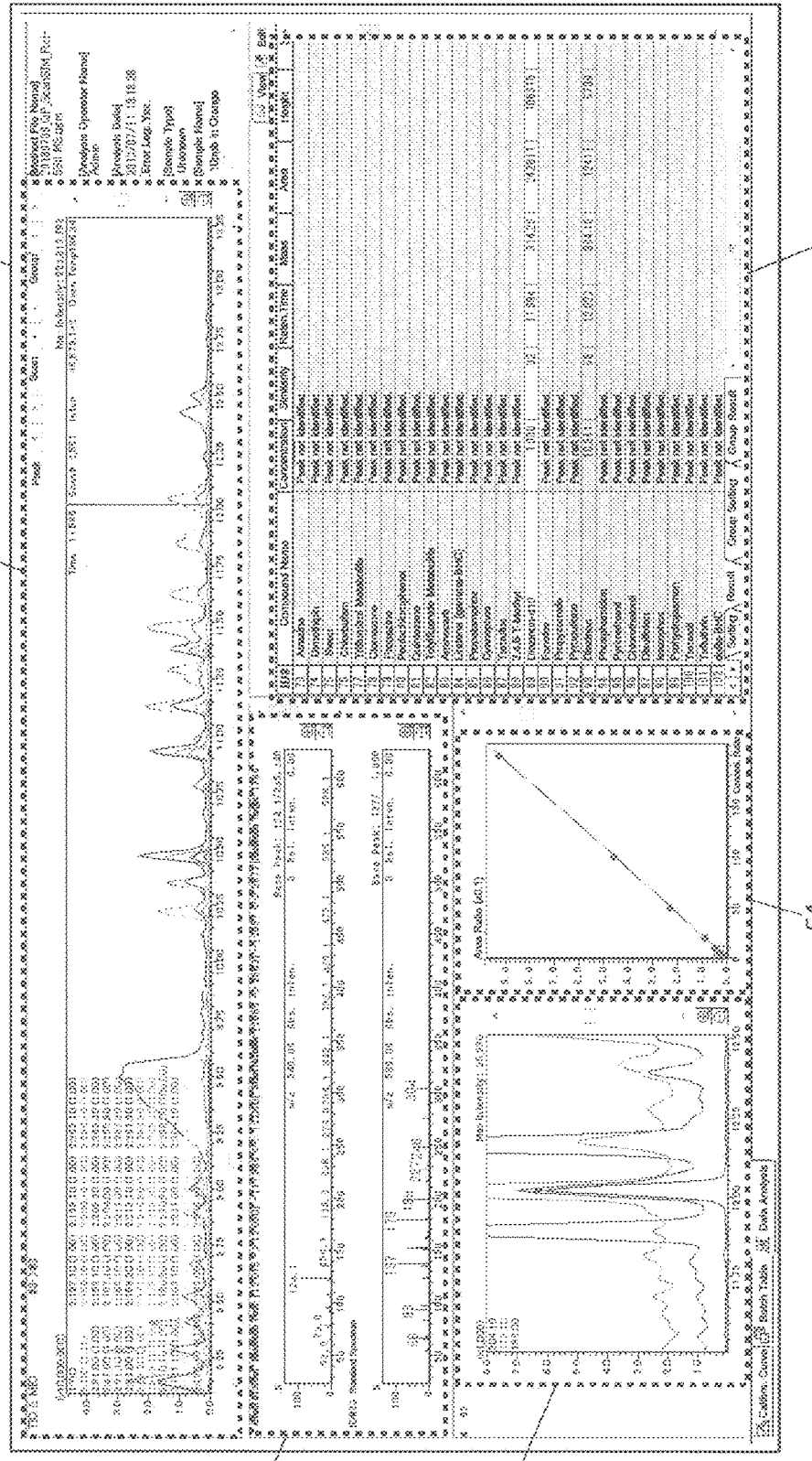
FIG. 4 is a display window showing the result of an actual measurement in which the quantity of diazinon was determined using diazinon-d10 as the surrogate.
Figure 5:
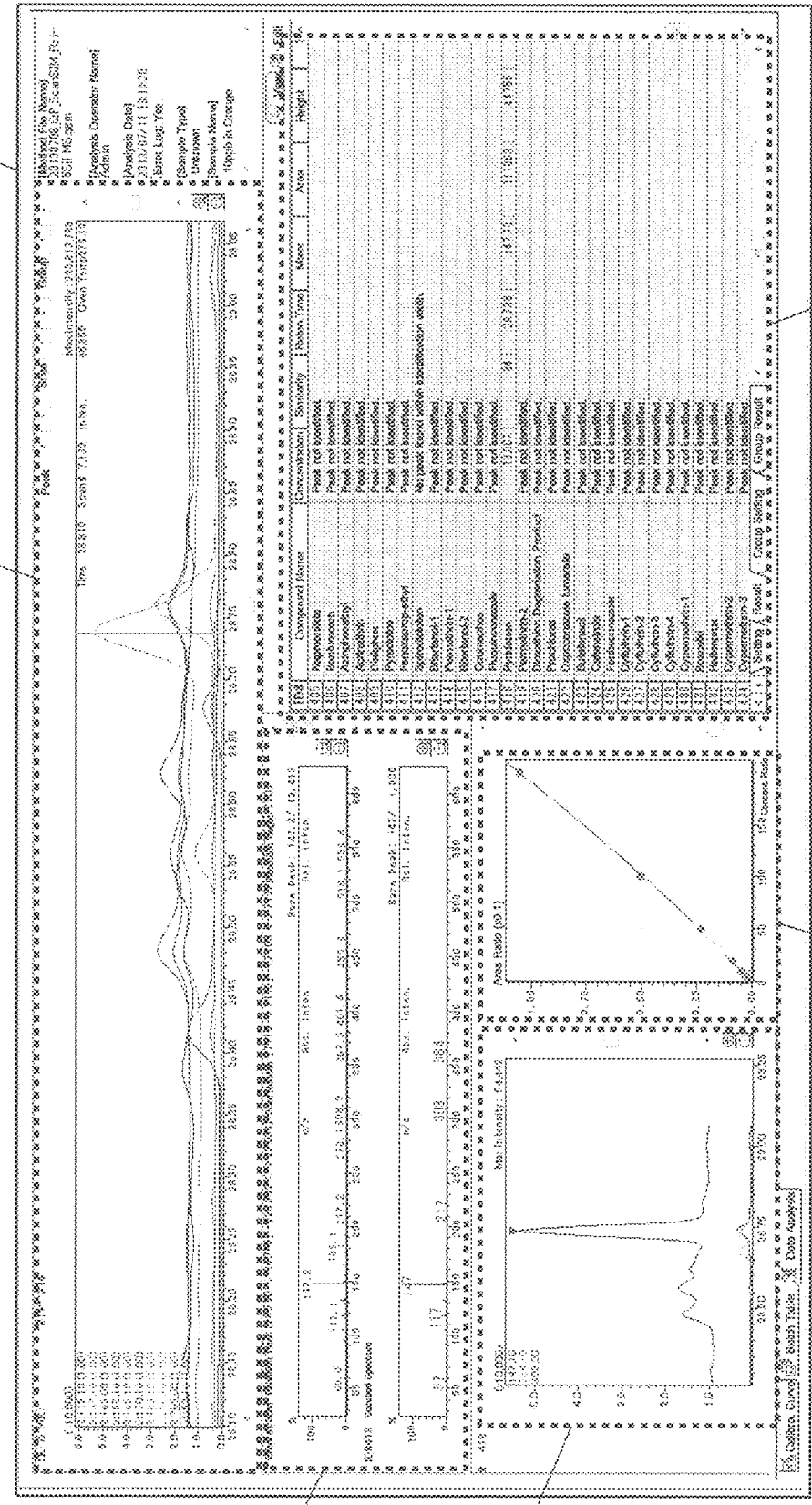
FIG. 5 is a display window showing the result of an actual measurement in which the quantity of pyridaben was determined using diazinon-d10 as the surrogate.

FIG. 4 is the result of the quantitative analysis of diazinon performed using diazinon-d10 as the internal standard substance. FIG. 5 is the result of the quantitative analysis of pyridaben performed using diazinon-d10 as the internal standard substance. Each of FIGS. 4 and 5 is the display window showing the result of the quantitative analysis. The display window 50 includes: a chromatogram display area 51 (uppermost) for showing a chromatogram (total ion chromatogram or mass chromatogram); a spectrum display area 52 (middle left) for showing mass spectra at an arbitrary point in time on the chromatogram; a chromatogram enlargement display area 53 (lower left); a calibration curve display area 54 (lower middle) used for the quantitative determination; and a quantitative determination result table 55 (middle and lower right) for listing the results of the quantitative determination for analytes.

The result shown in the quantitative determination result table 55 in FIG. 4 demonstrates that both diazinon-d10 as the surrogate (internal standard substance) and diazinon as the analyte have been identified. The calibration curve shown in the calibration curve display area 54 in FIG. 4 demonstrates that there is a linear relationship between the concentration ratio and the area ratio. This is the natural result, since the compound used as the internal standard substance is the deuterated form of the analyte (diazinon) and can be practically regarded as diazinon itself. By determining the concentration by comparing the measured value of the peak area ratio with this calibration curve, a highly accurate quantitative determination can be achieved.

On the other hand, the quantitative determination result table 55 in FIG. 5 demonstrates that pyridaben as the analyte has been identified. As regards the calibration curve shown in the calibration curve display area 54 in FIG. 5, although the relationship between the concentration ratio and the area ratio is slightly non-linear as compared to the calibration curve shown in FIG. 4, the overall relationship has a sufficiently high degree of linearity; in particular, the curve is virtually straight within a range where the concentration ratio is low. Accordingly, the quantity of pyridaben can also be determined with a high level of accuracy by determining the concentration by comparing the measured value of the peak area ratio with this calibration curve.

Additionally, for various other residual agricultural chemicals which are subject to control under the Positive List, it was similarly confirmed that a sufficiently high level of quantitative accuracy can be secured when the quantitative determination is performed by the internal standard method using, as the surrogate, a compound obtained by the deuteration of a different compound included in the same group. Thus, by the previously described multicomponent quantitative analysis method using the GC/MS, it is possible to easily and conveniently perform high-accuracy quantitative determinations for a large number of compounds.

It should be noted that the previous embodiment is a mere example of the present invention, and any change, modification or addition appropriately made without departing from the spirit of the present invention will evidently fall within the scope of claims of the present application.

For example, although the previously described embodiment is concerned with a multicomponent quantitative analysis method using a GC/MS, the present invention is also applicable in a gas chromatograph which does not use a mass spectrometer as the detector, if the GC column is capable of fully separating all substances. The present invention is also applicable in a liquid chromatograph or a liquid chromatograph mass spectrometer in which the component separation is achieved based primarily on the difference in their polarity.

REFERENCE SIGNS LIST

1 . . . Gas Chromatograph
10 . . . Sample Vaporization Chamber
11 . . . Micro-Syringe
12 . . . Column Oven
13 . . . Column
2 . . . Mass Spectrometer
20 . . . Analysis Chamber
21 . . . Ion Source
22 . . . Ion Lens
23 . . . Quadrupole Mass Filter
24 . . . Detector
3 . . . Data Processing Unit
30 . . . Data Storage Section
31 . . . Chromatogram Creator
32 . . . Peak Detector
33 . . . Peak Area Ratio Calculator
34 . . . Quantitative Determination Processor
35 . . . Calibration Curve Database
4 . . . Analysis Control Unit
5 . . . Central Control Unit
6 . . . Input Unit
7 . . . Display Unit
8 . . . Simultaneous Multicomponent Quantitative Determination Control Program
50 . . . Display Window
51 . . . Chromatogram Display Area
52 . . . Spectrum Display Area
53 . . . Chromatogram Enlargement Display Area
54 . . . Calibration Curve Display Area
55 . . . Quantitative Determination Result Table

The invention claimed is:

1. A multicomponent quantitative analysis method using a chromatograph for determining quantities of a number of compounds contained in a sample using the chromatograph, the method comprising following steps:

at least a portion of a number of analytes which may possibly be contained in a sample to be analyzed is divided into a plurality of groups based on at least either an elution position determined by silica gel column chromatography under a same condition or a partition ratio in a hexane-acetonitrile partition method, and a different surrogate is designated for each group;

the surrogate is added to a standard sample for a creation of calibration curves as a common internal standard substance for analytes included in each group, a chromatographic analysis of the standard sample is performed, and a calibration curve to be used for a quantitative determination of the analytes by an internal standard method is created based on a result of the chromatographic analysis; and in a quantitative determination of analytes contained in an unknown sample, the plurality of surrogates are added to the unknown sample, a chromatographic analysis of the unknown sample is performed, and a result of this chromatographic analysis is compared with the corresponding calibration curves to determine the quantities of the analytes.

2. The multicomponent quantitative analysis method using a chromatograph according to claim 1, wherein at least a portion of a number of analytes which may possibly be contained in a sample to be analyzed is divided into a plurality of groups based on relative values of the elution position of each analyte and the elution positions of the surrogates and/or relative values of the partition ratio of each analyte and the partition ratios of the surrogates.

3. The multicomponent quantitative analysis method using a chromatograph according to claim 1, wherein the surrogate assigned to each group is a compound obtained by a stable-isotope labeling of a compound which is one of the analytes included in that group.

4. The multicomponent quantitative analysis method using a chromatograph according to claim 2, wherein the surrogate assigned to each group is a compound obtained by a stable-isotope labeling of a compound which is one of the analytes included in that group.

* * * * *